United States Patent
Huber et al.

(10) Patent No.: US 11,474,092 B2
(45) Date of Patent: Oct. 18, 2022

(54) METHOD FOR DETERMINING PROPERTIES OF A HYDROCARBON-CONTAINING GAS MIXTURE AND DEVICE FOR THE SAME

(71) Applicant: Endress+Hauser Flowtec AG, Reinach (CH)

(72) Inventors: Christof Huber, Bern (CH); Patrick Reith, Putzbrunn (CH); Anastasios Badarlis, Birsfelden (CH)

(73) Assignee: ENDRESS+HAUSER FLOWTEC AG, Reinach (CH)

( * ) Notice: Subject to any disclaimer, the term of this patent is extended or adjusted under 35 U.S.C. 154(b) by 510 days.

(21) Appl. No.: 16/348,139

(22) PCT Filed: Oct. 10, 2017

(86) PCT No.: PCT/EP2017/075798
§ 371 (c)(1),
(2) Date: May 7, 2019

(87) PCT Pub. No.: WO2018/082875
PCT Pub. Date: May 11, 2018

(65) Prior Publication Data
US 2019/0360990 A1 Nov. 28, 2019

(30) Foreign Application Priority Data
Nov. 7, 2016 (DE) ..................... 10 2016 121 226.1

(51) Int. Cl.
*G01N 9/36* (2006.01)
*G01N 33/22* (2006.01)
(Continued)

(52) U.S. Cl.
CPC ......... *G01N 33/225* (2013.01); *G01N 1/2247* (2013.01); *G01N 9/32* (2013.01);
(Continued)

(58) Field of Classification Search
CPC .......... G01N 1/2247; G01N 9/32; G01N 9/36; G01N 33/225; G01N 2291/0215;
(Continued)

(56) References Cited

U.S. PATENT DOCUMENTS 5,235,844 A * 8/1993 Bonne .................. G01N 29/036
 374/36
5,486,107 A 1/1996 Bonne
(Continued)

FOREIGN PATENT DOCUMENTS

CN 101398420 A 4/2009
CN 101571500 A 11/2009
(Continued)

OTHER PUBLICATIONS

Search Report for German Patent Application No. 10 2016 121 226.1, German Patent Office, dated Jul. 11, 2017, 7 pp.
(Continued)

*Primary Examiner* — Alexander A Mercado
(74) *Attorney, Agent, or Firm* — Kelly J. Smith; Endress+Hauser (USA) Holding Inc.

(57) ABSTRACT

A method for determining properties of a hydrocarbon-containing gas mixture includes determining a thermal conductivity value, density measurement, viscosity measurement, and temperature and pressure. The method also includes determining a hydrogen content of the gas mixture on the basis of the thermal conductivity value and the temperature and pressure, determining a density measurement and associated temperature and pressure, and determining the mean molar mass or standard density on the basis of the density measurement and the temperature and pressure. The method further includes determining the mean molar mass or standard density of a hydrogen-free residual gas mixture based on the mean molar mass or standard (Continued)

density and the hydrogen fraction, determining the Wobbe index of the residual gas mixture based on the viscosity measurement and the temperature and pressure, and determining a calorific value based on the mean molar mass or standard density and the Wobbe index.

12 Claims, 6 Drawing Sheets (51) Int. Cl.
G01N 1/22 (2006.01)
G01N 9/32 (2006.01)
G06F 17/00 (2019.01)

(52) U.S. Cl.
CPC ............... *G01N 9/36* (2013.01); *G06F 17/00* (2013.01); *C10L 2290/60* (2013.01); *G01N 2291/0215* (2013.01); *G01N 2291/02809* (2013.01); *G01N 2291/02818* (2013.01); *G01N 2291/02872* (2013.01); *G01N 2291/02881* (2013.01)

(58) Field of Classification Search
CPC .......... G01N 2291/02809; G01N 2291/02818; G01N 2291/02872; G01N 2291/02881
See application file for complete search history.

(56) References Cited

U.S. PATENT DOCUMENTS

| | | | |
|---|---|---|---|
| 6,047,589 A | 4/2000 | Hammond et al. | |
| 2004/0261497 A1* | 12/2004 | Thurston | G01N 33/225 |
| | | | 73/23.2 |
| 2010/0224834 A1* | 9/2010 | Peng | G01N 9/36 |
| | | | 252/372 |
| 2011/0098936 A1* | 4/2011 | Bats | G01N 9/36 |
| | | | 702/24 |
| 2018/0038811 A1* | 2/2018 | Hornung | G01N 25/005 |
| 2018/0306764 A1* | 10/2018 | Huber | G01N 29/024 |
| 2019/0360990 A1* | 11/2019 | Huber | G01N 9/36 |
| 2020/0041479 A1* | 2/2020 | Huber | F02D 41/0027 |

FOREIGN PATENT DOCUMENTS

| | | | | |
|---|---|---|---|---|
| CN | 102138066 A | 7/2011 | | |
| CN | 104279084 A | 1/2015 | | |
| CN | 105593671 A | 5/2016 | | |
| CN | 105606786 A | 5/2016 | | |
| DE | 1017735 A1 | 10/1957 | | |
| DE | 2928739 B1 | 6/1980 | | |
| DE | 19900129 A1 | 8/2000 | | |
| DE | 69231977 T2 | 4/2002 | | |
| DE | 102014106729 A1 | 11/2015 | | |
| EP | 3021117 A1 | 2/1989 | | |
| EP | 0967483 A2 | 12/1999 | | |
| EP | 1193488 A2 | 4/2002 | | |
| EP | 2015056 A1 * | 1/2009 | ............. | G01N 33/22 |
| EP | 2042850 A2 | 4/2009 | | |
| EP | 2993472 A1 | 3/2016 | | |
| EP | 3021117 A1 * | 5/2016 | ............... | G01F 1/66 |
| GB | 2296091 A | 6/1996 | | |
| WO | 2009152819 A1 | 12/2009 | | |
| WO | 2013092104 A1 | 6/2013 | | |

OTHER PUBLICATIONS

Search Report for International Patent Application No. PCT/EP2017/075798, WIPO, dated Nov. 27, 2017, 14 pp.
Gasbeschaffenheit, Technische Regel—Arbeitsblatt, DVGW Regelwerk, Mar. 2013, 8 pp.
https://shop.wvgw.de/G-260-Technical-Rule-09-2021/511831, G 260 Technical Rule Sep. 2021-Gas Quality, 29 pp.

* cited by examiner

METHOD FOR DETERMINING PROPERTIES OF A HYDROCARBON-CONTAINING GAS MIXTURE AND DEVICE FOR THE SAME

CROSS-REFERENCE TO RELATED APPLICATIONS

The present application is related to and claims the priority benefit of German Patent Application No. 10 2016 121 226.1, filed on Nov. 7, 2016 and International Patent Application No. PCT/EP2017/075798 filed on Oct. 10, 2017, the entire contents of which are incorporated herein by reference.

TECHNICAL FIELD

The present invention relates to a method for determining the properties of a hydrocarbon-containing gas mixture and an apparatus therefor. The relevant gas mixtures are, in particular, natural gas or biogas.

BACKGROUND

Natural gas is a fossil fuel. It has a storage-facility-dependent composition. The principal constituent of natural gas is methane, with a molar fraction of, for example, 75% to 99%. Natural gas frequently also contains larger fractions of ethane (1% to 15%), propane (1% to 10%), butane, and ethene. Further minor constituents are hydrogen sulfide, nitrogen, carbon dioxide, and water vapor.

Biogas is a combustible gas mixture of varying composition which is produced by fermentation of biomass of any type. In the crude state, it contains, in particular, methane (up to 60%) and carbon dioxide as main constituents. Also included are nitrogen, oxygen, hydrogen sulfide, water vapor, and ammonia. Hydrogen sulfide and ammonia must be removed before burning or before feeding into the natural gas network. It is also advantageous to remove carbon dioxide before combustion.

In order to be able to reliably control combustion processes, it is necessary to quickly recognize the current calorific value of a gas mixture that is being fed directly to a process.

The Wobbe index W, which is defined as the quotient of the calorific value per unit volume H and the root of the relative density, serves as a technically more relevant characterization of the calorific value. The relative density is the quotient of the density $\rho$ of the fuel gas and the density of dry air $\rho_0$ under the same pressure and temperature conditions:

$$W = \frac{H}{\sqrt{\frac{\rho}{\rho_0}}}$$

Gas mixtures of natural gas having the same Wobbe index can easily be exchanged during operation of a burner. Instead of comparing the density gradient, the equivalent coefficient of the mean molar masses of the gas and dry air can also be used.

The patent specifications, DE 69 231 977 T2 and U.S. Pat. No. 5,311,447 A1, disclose methods for determining the calorific value of a gas mixture from the thermal conductivity, the heat capacity, the optical absorption, and the viscosity of the gas mixture.

Publication GB 2 296 091 A describes a method for determining the calorific value or the Wobbe index of a gas mixture on the basis of its thermal conductivity, density, viscosity, and sound velocity. MEMS AG, under the designation Gas QS, offers a sensor which, on the basis of the thermal conductivity, the heat capacity, and the density of a gas mixture, determines its calorific value or Wobbe index.

The still unpublished patent application DE 102015117468.5 discloses a method for the method for determining the Wobbe index or the calorific value as well as the inert gas fraction of gas mixtures that have, in particular, natural gas or biogas, on the basis of the viscosity and the density or sound velocity.

However, the gas network increasingly serves as an energy store for alternatively generated gas from "Power to Gas" ($H_2$) and "Biogas" ($CH_4+CO_2$) enriched with liquid petroleum gas ($C_2H_6+C_3H_8$). This significantly changes the gas composition in the network. The gas quality that reaches the consumer fluctuates widely, and fast changes can occur. The hydrogen fraction can be up to 20%. The Wobbe index is suitable only to a limited extent as a measure for good burner control, because $H_2$ behaves differently than natural gas.

SUMMARY

There is therefore a need for a simple, robust, and reliable method and corresponding measuring devices for determining properties of a gas mixture, in particular, its calorific value, when it contains hydrogen. It is therefore an aim of the present invention to provide such a method and such an apparatus.

The aim is achieved according to the invention by the method according to independent claim 1 and the device according to independent claim 11.

The method according to the invention for determining properties of a hydrocarbon-containing gas mixture which, in particular, has natural gas or biogas comprises:

allowing the gas mixture to flow through a measuring arrangement;

determining a pressure- and temperature-dependent thermal conductivity value, an associated temperature measurement, and an associated pressure measurement of the flowing gas mixture;

determining a hydrogen fraction $X_{H2}$ of the gas mixture on the basis of the thermal conductivity value, the associated temperature measurement, and the associated pressure measurement;

determining a pressure- and temperature-dependent density measurement of an associated temperature measurement and of an associated pressure measurement of the flowing gas mixture;

determining a value for the mean molar mass or the standard density of the gas mixture on the basis of the density measurement, the associated temperature measurement, and the associated pressure measurement;

determining a value for the mean molar mass or the standard density of a residual gas mixture reduced by the hydrogen fraction on the basis of the mean molar mass of the gas mixture and of the hydrogen fraction;

determining a pressure-dependent and temperature-dependent viscosity measurement, an associated temperature measurement, and an associated pressure measurement of the flowing gas mixture;

determining a value for the Wobbe index of the residual gas mixture on the basis of the viscosity measurement, the associated pressure measurement, and the associated temperature measurement; and determining a first value $CV_W$ for the calorific value of the residual gas mixture on the basis of the mean molar mass or the standard density of the residual gas mixture and of the Wobbe index of the residual gas mixture.

In a further development of the invention, the method further comprises determining the inert gas fraction of the residual gas mixture on the basis of the first value for the calorific value and the mean molar mass or the standard density of the residual gas mixture.

In a further development of the invention, the determination of the inert gas fraction comprises the following steps:

determining a second value $CV_M$ for the calorific value on the basis of the mean molar mass or the standard density of the residual gas mixture by means of a function which is independent of the viscosity or the Wobbe index; and determining the inert gas fraction as a function of the first value for the calorific value of the residual gas mixture and the second value for the calorific value of the residual gas mixture.

The determination of the heat conductivity value $\lambda$ at a given pressure and a given temperature is followed in one embodiment of the invention by a conversion into a standard heat conductivity $\lambda_{ref}$ under standard conditions, e.g., with a polynomial in $\lambda$, $\rho$, and T, in particular, $$\lambda_{ref} = \Sigma A_i \cdot T^{ti} \cdot \lambda^{li} \cdot p^{vi},$$

wherein i=0 . . . k is an index of the summands, and the $A_i$ of its coefficients as well as $t_i$, $l_i$, and $v_i$ are whole number exponents. For example:

$$\lambda_{ref} = A_0 + A_1 \cdot T + A_2 \cdot T^2 + A_3 \cdot p + A_4 \cdot \lambda + A_5 \cdot \lambda \cdot T.$$

In one embodiment of the invention, the hydrogen fraction $X_{H2}$ is calculated as a function of the standard heat conductivity.

Determining the mean molar mass M of the gas mixture in one embodiment of the invention comprises calculating the mean molar mass as a function of density, pressure, and temperature, $$M = f(\rho, T, p),$$

e.g., by means of a polynomial in $\rho$, p, and T, i.e., $$M = \Sigma B_i \cdot T^{ti} \cdot \rho^{ri} \cdot p_{vi},$$

wherein i=0 . . . k is an index of the summands, and the $B_i$ of its coefficients as well as $t_j$, $r_i$, and $v_i$ are whole number exponents.

For example:

$$B_0 + B_1 \cdot \rho \cdot T/p + B_2 \cdot \rho^2 \cdot T/p + B_3 \cdot \rho^2/p + B_4 \cdot (\rho \cdot T/p)^2 + B_5 \cdot p$$

The mean molar mass $M_R$ of the residual gas mixture can be calculated from the mean molar mass and its hydrogen fraction $X_{H2}$ as:

$$M_R = (M - X_{H2} \cdot M_{H2})/(1 - X_{H2}),$$

wherein $M_{H2}$ is the molar mass of hydrogen.

In a further development of the invention, the determination of the value for the Wobbe index is preceded by the determination of a standard viscosity value of the flowing gas mixture that the flowing gas mixture would have at a standard temperature and a standard pressure, on the basis of the viscosity measurement, the associated temperature measurement, and the associated pressure measurement, wherein the Wobbe index is determined by means of the standard viscosity value of the gas mixture. The standard viscosity resp. standard viscosity can be determined, for example, with a polynomial in $\eta$, p, $\rho$, and T, i.e., $$\eta_{ref} = \Sigma C_i \cdot T^{ti} \cdot p^{vi} \cdot \eta^{ni} \cdot \rho^{ri},$$

wherein i=0 . . . k is an index of the summands, and the $C_i$ of its coefficients as well as $t_i$, $v_i$, $n_i$, and $r_i$ are whole number exponents. For example:

$$\eta_{ref} = C_0 + C_1 \cdot \eta + C_2 \cdot p + C_3 \cdot T + C_4 \cdot T^2.$$

In an embodiment of this further development of the invention, the Wobbe index is calculated with a polynomial, in particular, a square or linear function of the standard viscosity value according to:

$$W = \Sigma A_i \cdot \eta_{ref}^{ni},$$

wherein i=0 . . . k is an index of the summands, and the $A_i$ of its coefficients as well as $n_i$ are whole number exponents.

For example:

$$W = A_0 + A_1 \eta_{ref}.$$

The first value $CV_W$ for the calorific value of the residual gas may be calculated according to an embodiment of the invention as the product of the Wobbe index with the root from the quotient of the mean molar mass of the residual gas divided by the mean molar mass of dry air, thus:

$$CV_W = W \cdot (M_R/M_{air})^{1/2}$$

The second value $CV_M$ for the calorific value of the residual gas can be calculated according to an embodiment of the invention as, in particular, a linear function of the mean molar mass M of the residual gas, for example:

$$CV_M = D_0 + M_R \cdot D_1,$$

wherein the $D_i$ are constants.

In a further development of the invention, the inert gas fraction $X_{inert-R-C}$ in the residual gas is determined on the basis of a ratio between the second value for the calorific value of the residual gas and the first value for the calorific value of the residual gas, e.g., $$X_{inert-R-C} = E \cdot (CV_M/CV_W - 1),$$

wherein E is a constant.

In a further development of the invention, the method further comprises determining a value for the inert gas fraction)(inert of the flowing gas mixture on the basis of the value for the inert gas fraction of the residual gas mixture $X_{inert-R}$ and the hydrogen fraction $X_{H2}$, e.g., according to $$X_{inert} = X_{inert-R} \cdot (1 - X_{H2}).$$

In a further development of the invention, the method further comprises determining a value for the calorific value of the flowing gas mixture on the basis of the value for the hydrogen fraction, of the specific calorific value of hydrogen, and of the calorific value of residual gas mixture, e.g., according to $$CV_{total} = CV_W \cdot (1 - X_{H2}) + CV_{H2} \cdot X_{H2}.$$

In a further development of the invention, determining the inert gas fraction takes place under the assumption that the inert gas substantially comprises carbon dioxide and nitrogen.

In a further development of the invention, to determine the molar mass of the flowing gas mixture, a value for the standard density value for the density of the flowing gas is first determined under standard conditions on the basis of the pressure- and temperature-dependent density measurement of the associated temperature measurement and of the associated pressure measurement of the flowing gas mixture.

In a further development of the invention, the viscosity and the density of the gas mixture are determined by means of a vibronic sensor, wherein the vibronic sensor is, in particular, a MEMS sensor which has at least one oscillating measuring tube that is flowed through and/or at least one oscillator surrounded by the flowing gas mixture, in particular, in the form of at least one oscillating cantilever or an oscillating tuning fork.

The device according to the invention for determining properties of a hydrocarbon-containing gas mixture, in particular, with a method according to the invention, comprises: a measuring arrangement through which the gas mixture can flow, having a temperature sensor, a pressure sensor, and a vibronic sensor for determining a viscosity measurement and, in some cases, a density measurement of the flowing gas mixture; a thermal conductivity sensor; and an evaluation unit for calculating properties of the flowing gas mixture.

In a further development of the invention, the vibronic sensor is a MEMS sensor which has at least one flow-through, oscillatable measuring tube and/or at least one oscillator surrounded by the flowing gas mixture, in particular, in the form of at least one oscillatable cantilever or an oscillatable tuning fork.

BRIEF DESCRIPTION OF THE DRAWING

The invention is explained in the following in further detail on the basis of the exemplary embodiments shown in the figures.

FIG. 4b shows a diagram of the energy content of residual gas mixtures cleaned of the hydrogen fraction on the basis of their Wobbe index illustrated in FIG. 4a;

FIG. 6b shows a flow diagram of an optional aspect of the exemplary embodiment from FIG. 6a;

DETAILED DESCRIPTION

Figure 1:
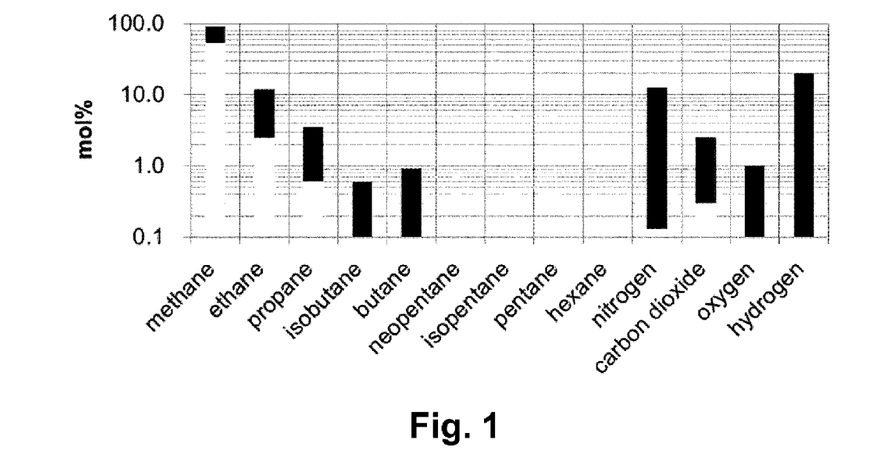
FIG. 1 shows a diagram of typical fuel gas compositions.

The invention is based upon the statistical analysis of the physical properties of several hundred samples of gas mixtures which contain natural gas and hydrogen supplemented by gas mixtures randomly generated within the range of the composition ranges illustrated in FIG. 1. The respective composition of the gas mixtures was determined by means of gas chromatography, or generated randomly, and, for the compositions determined, the physical properties of the gas mixtures were determined by calculation at various pressure and temperature values. In like manner, the physical properties of some pure gases were calculated. For the computational determination of the physical properties, a program of the NIST was used, viz., "Reference Fluid Thermodynamic and Transport Properties Database," or REFPROP for short, version 9.1, which is accessible at http://www.nist.gov/srd/nist23.cfm. An experimental determination of the physical quantities is also possible, but requires a greater effort. The physical quantities determined computationally include:

Density: $\rho(T,p)$
The mean molar mass: M
Dynamic viscosity: $\eta(T,p)$
Upper and lower calorific value, or calorific value and heating value CV
Wobbe index: $WI = CV/(M/M_{air})^{0.5}$ The development of the method according to the invention that is carried out on the basis of the above data is explained in more detail below.

FIG. 1 shows the range of typical molar fractions of pure gases in typical fuel gas mixtures. Besides the hydrocarbon-containing gases, it is also possible to identify nitrogen, carbon dioxide, oxygen, and up to 20% hydrogen.

Figure 2:
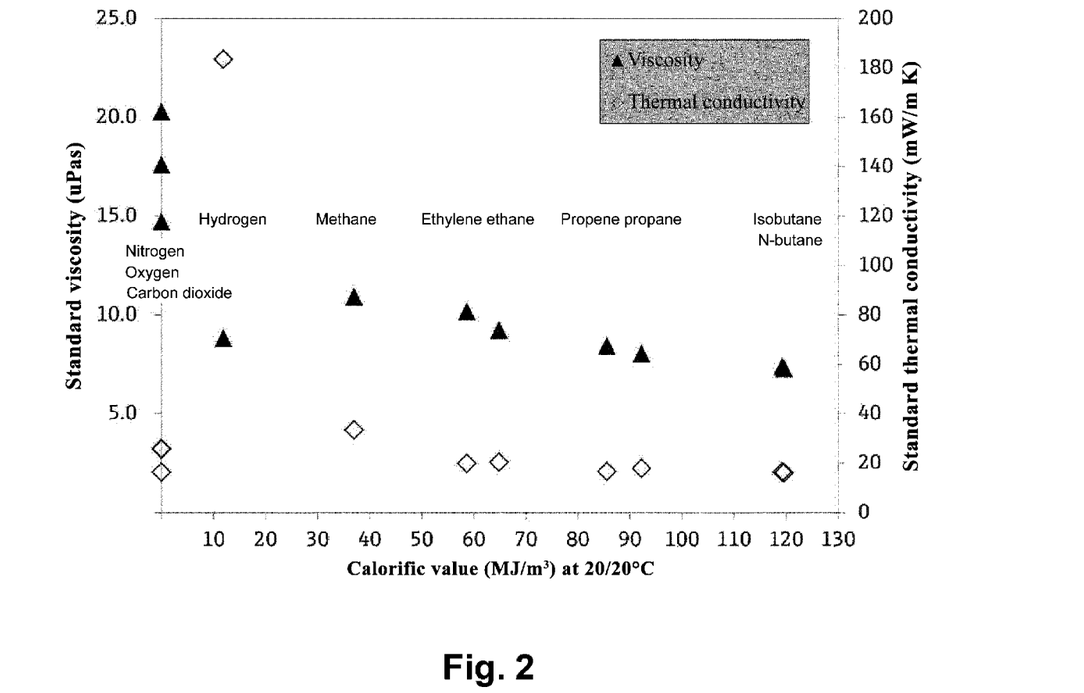
FIG. 2 shows a diagram of the standard viscosity and standard thermal conductivity of pure gases as a function of calorific value.

FIG. 2 shows the dynamic viscosity and the thermal conductivity of some pure gases as a function of their calorific value. The gases are nitrogen, oxygen, carbon dioxide, hydrogen, methane, ethylene, ethane, propene, propane, isobutane, and n-butane.

It can be seen that gases with a lower calorific value generally have a higher dynamic viscosity. However, this does not apply to hydrogen, which has a lower viscosity than methane, even though its calorific value is lower. In this respect, the viscosity cannot readily be used as a measurand for determining the calorific value. On the other hand, hydrogen has a considerably higher thermal conductivity than the other gases represented in FIG. 2. This therefore offers an approach based upon the thermal conductivity of a gas mixture for determining its hydrogen fraction, to exclude the hydrogen fraction from the gas mixture, and then to be able to calculate other properties for the residual gas mixture on the basis of the viscosity—for example, the Wobbe index or the calorific value.

Figure 3A:
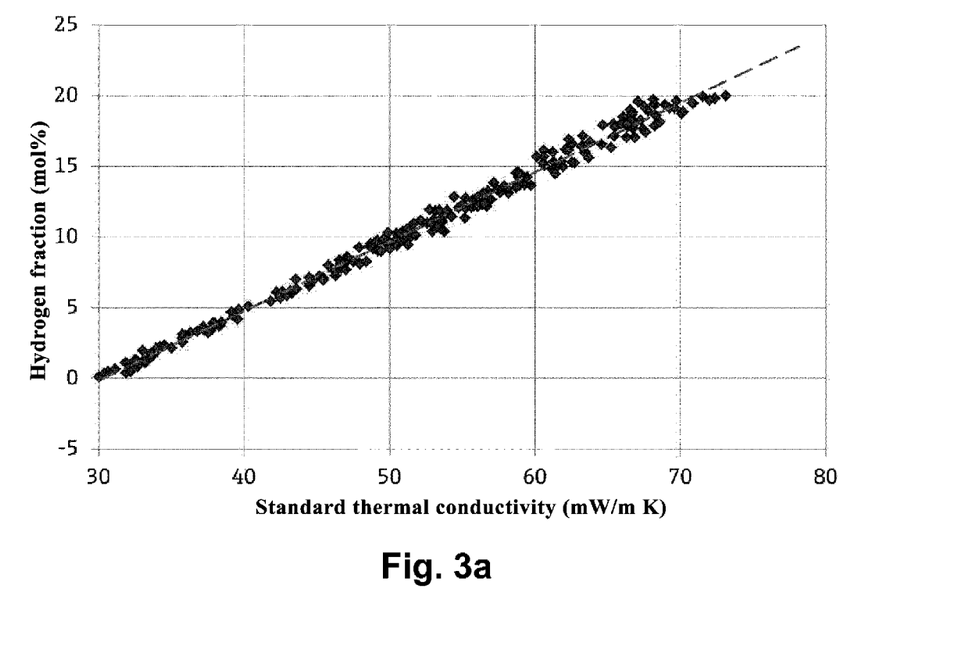
FIG. 3a shows a diagram of the hydrogen fraction of gas mixtures as a function of the standard heat conductivity.

As shown in FIG. 3a, the actual hydrogen fraction in mixtures of fuel gases correlates with the thermal conductivity. It should therefore be possible to represent the hydrogen fraction with sufficient accuracy as a function of the thermal conductivity, in particular, as a linear function of the thermal conductivity, wherein the latter is preferably first calculated as thermal conductivity under standard conditions in accordance with a polynomial in $\Delta$, p, and T, in particular, $$A_{ref} = A_0 + A_1 \cdot T + A_2 \cdot T^2 + A_3 \cdot p + A_4 \lambda + A_5 \cdot \lambda \cdot T, \tag{1}$$

wherein the $\lambda$ is the p, and T is measured thermal conductivity, and the $A_i$ are constants.

Figure 3B:
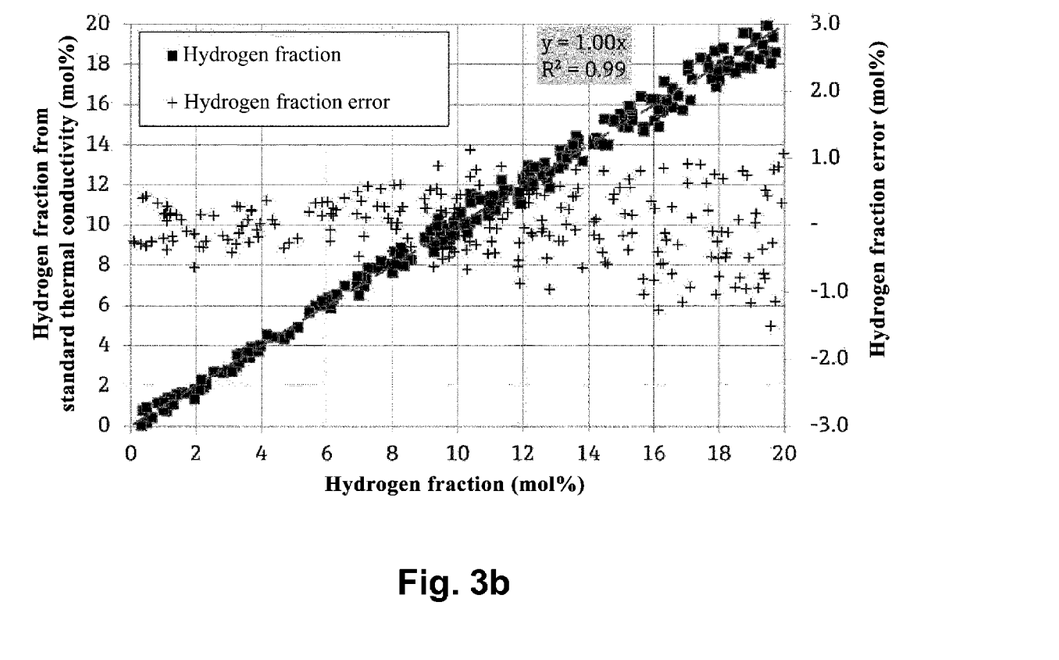
FIG. 3b shows a diagram of the hydrogen fraction of gas mixtures determined on the basis of the standard heat conductivity as a function of the actual hydrogen fraction.

This is confirmed by FIG. 3b, in which are depicted the hydrogen fraction calculated on the basis of the thermal conductivity by means of the above function, as well as the deviation between the calculated hydrogen fraction and actual hydrogen fraction, in each case as a function of the hydrogen fraction. The margin of error is sufficiently small for the purpose of characterizing a fuel gas.

Figure 4A:
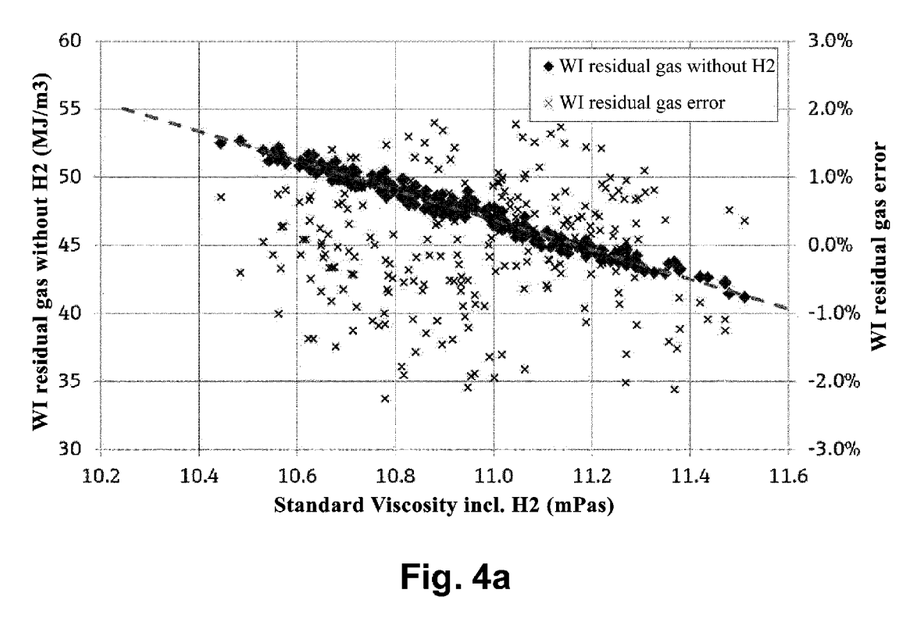
FIG. 4a shows a diagram of the Wobbe index of residual gas mixtures cleaned of the hydrogen fraction as a function of the standard viscosity of the gas mixtures containing the hydrogen fraction.
Figure 4B:
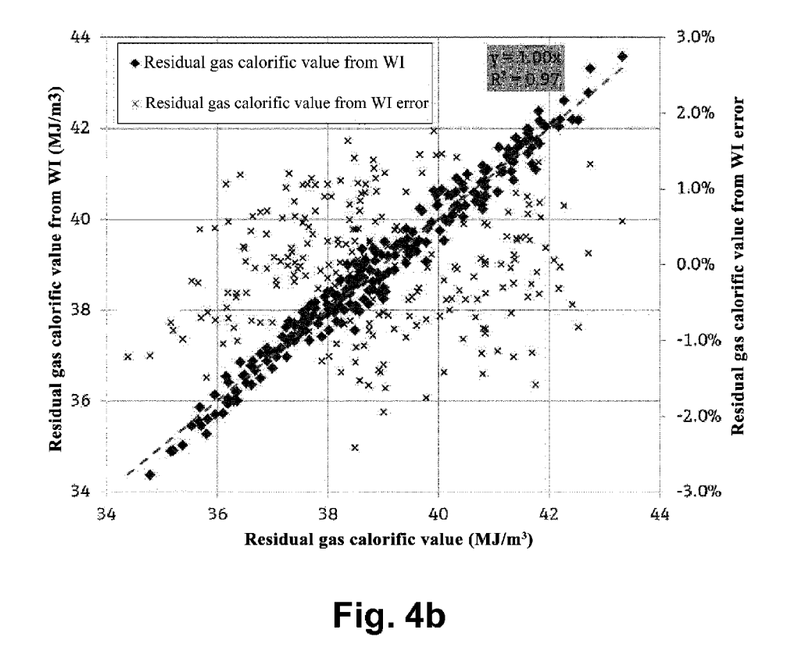

As already detailed in patent application DE 10 2015 117 468.5, the Wobbe index of a low-hydrogen fuel gas mixture correlates well with its viscosity. The investigations connected with the present invention have shown that the viscosity values for hydrogen-containing fuel gas mixtures correlate with the Wobbe index of the residual gas mixtures that are purified of the respective hydrogen fraction, as depicted in FIG. 4. The Wobbe index of the residual gas mixture purified of the hydrogen fraction can thus be determined on the basis of the dynamic viscosity of the entire flowing gas mixture.

It is advantageous first to determine a standard viscosity under standard conditions $n_{ref}$ from a current viscosity value $\eta(T,p)$ at a given pressure p and a given temperature T, wherein the Wobbe index must then be calculated on the basis of the standard viscosity under standard conditions. The default viscosity $\eta_{ref}$ is to be calculated from a current viscosity value, e.g., with a polynomial in $\eta$, p, and T, in particular:

$$\eta_{ref} = C_0 + C_1 \cdot \eta + C_2 \cdot p + C_3 \cdot T + C_4 \cdot T^2 \qquad (2)$$

wherein the $C_i$ are constants.

The Wobbe index W for the residual gas mixture is then determined as a linear function of the standard viscosity, i.e., $$W = A\eta_{ref} + B, \qquad (3),$$

wherein A and B are constants.

From the Wobbe index for the residual gas mixture cleaned of the hydrogen fraction and determined on the basis of the viscosity measurement, its calorific value can be determined by multiplication with the square root of its specific weight, i.e., $$CV_w = W \cdot (M_R/M_{air})^{1/2} \qquad (4)$$

The mean molar mass $M_R$ of the residual gas mixture required for the calculation is determined on the basis of the density of the gas mixture and its hydrogen fraction.

$$M = B_0 + B_1 \cdot \rho \cdot T/p + B_2 \cdot \rho^2 \cdot T/p + B_3 \cdot \rho^2/p + B_4 \cdot (\rho \cdot T/p)^2 + B_5 \cdot p, \qquad (5)$$

wherein the $B_i$ are constants.

The mean molar mass $M_R$ of residual gas mixture can be calculated from the mean molar mass and its hydrogen fraction $X_{H2}$ as:

$$M_R = (M - X_{H2} \cdot M_{H2})/(1 - X_{H2}), \qquad (6)$$

wherein $M_{H2}$ is the molar mass of hydrogen.

With the mean molar mass MR of the residual gas mixture thus determined, its calorific value can now be determined as $CV_w$ on the basis of the Wobbe index in accordance with equation 2.

On the other hand, the calorific value of a gas mixture shows a good correlation to its specific weight as long as the inert gases, nitrogen and carbon dioxide, do not play a role. In this case, the calorific value $CV_M$ can be estimated well on the basis of the mean molar mass with $$CV_M = D_0 + M \cdot D_1 \qquad (7),$$

wherein the $D_i$ are constants.

However, if the inert gases include nitrogen and carbon dioxide, the correlation is no longer valid, and the calorific value is overestimated. This makes the present invention useful for calculating a the fraction of inert gases $X_{inert-R-C}$ in the residual gas mixture, using the deviation between the calorific value on the basis of the viscosity and the calorific value based exclusively upon the mean molar mass, in accordance with $$X_{inert-R-C} = E \cdot (CV_M/CV_W - 1), \qquad (8)$$

wherein E is a constant.

Figure 5:
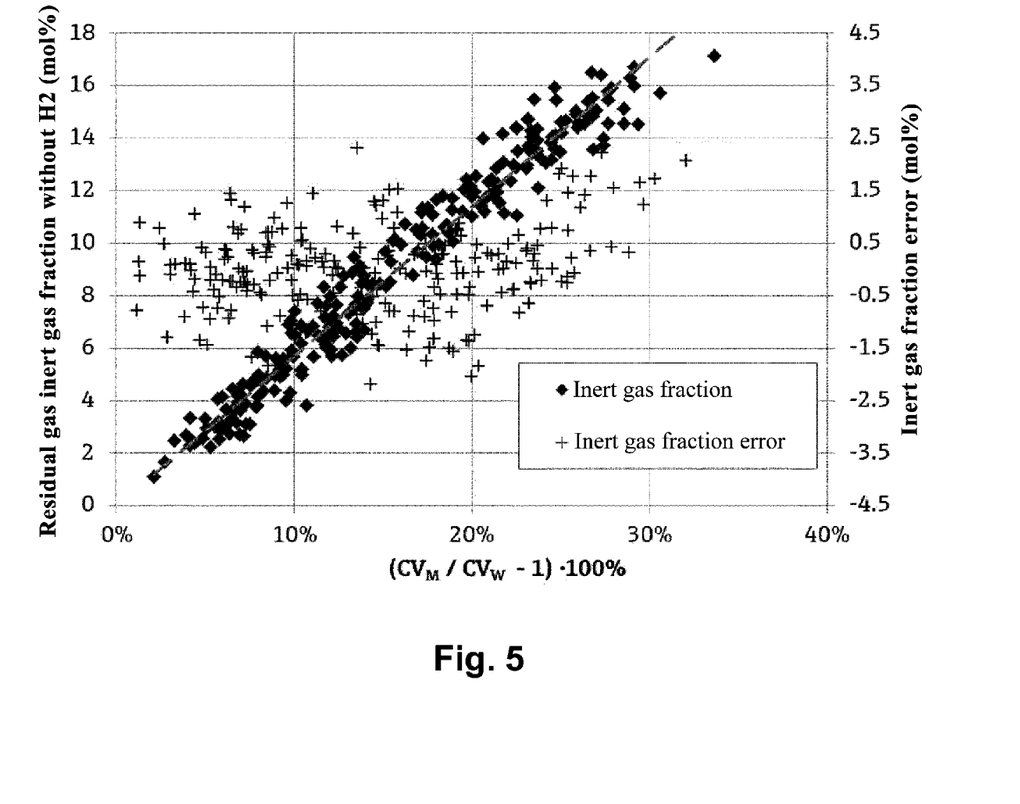
FIG. 5 shows a correlation diagram of the actual content of carbon dioxide and nitrogen of different residual gas mixtures as a function of the deviation between the calorific values determined by means of correlation calculation, taking into account the viscosity value, and the calorific values of the residual gas mixtures determined by means of correlation calculation, without taking into account the viscosity value.

It can be seen from FIG. 5 that this is a valid approach for determining the inert gas fraction $X_{inert-R}$ in the residual gas mixture. The diamonds show the actual inert gas fraction $X_{inert-R}$ as a function of the deviation of the calorific values of the residual gas mixture $CV_M/CV_W - 1$. The slope of the mean straight line plotted in the diagram corresponds to the above constant E. The crosses indicate the relative error of the inert gas fraction $X_{inert-R-C}$ calculated according to the above equation, respectively in relation to the actual $X_{inert-R}$. As a result, the proposed procedure for calculating the inert gas fraction is satisfactory. The inert gas fraction based upon the total gas mixture is calculated as $$X_{inert} = X_{inert-R-C} \cdot (1 - X_{H2}). \qquad (9)$$

The calorific value of the total gas mixture $CV_{total}$ is calculated in accordance with $$CV_{total} = CV_W \cdot (1 - X_{H2}) + CV_{H2} \cdot X_{H2}. \qquad (10)$$

The gas mixture is comprehensively characterized with the calculated parameters.

Figure 6A:
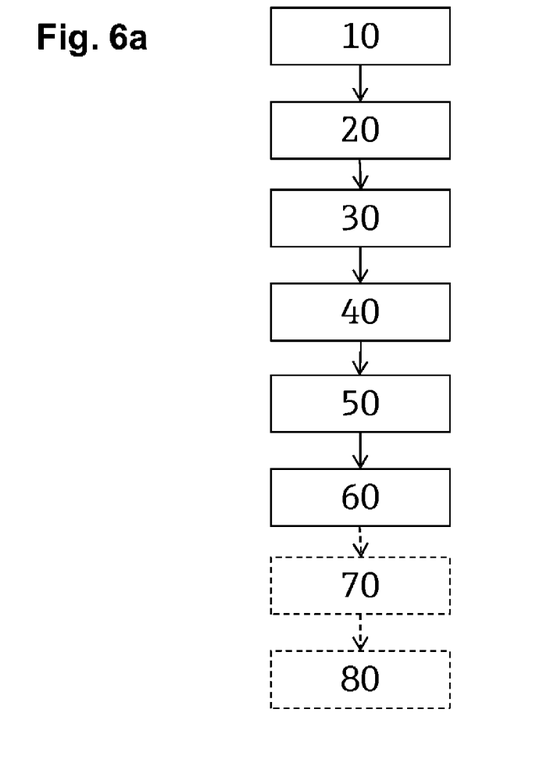
FIG. 6a shows a flow diagram of an exemplary embodiment of the method according to the present disclosure.
Figure 6B:
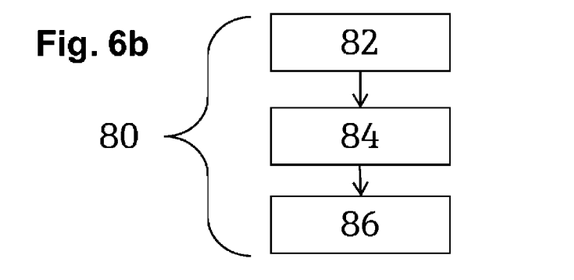

In summary, FIG. 6 shows a flow diagram of an exemplary embodiment of the method according to the invention.

An exemplary embodiment of the method according to the invention shown in FIGS. 6a and 6b comprises, in a step 10, the detection of a thermal conductivity measurement, a density measurement, a viscosity measurement $\eta$, a temperature measurement T, and a pressure measurement p of the flowing gas mixture, wherein said measurements are to be detected as simultaneously as possible, and the sensors required therefor are preferably arranged as closely together as possible, so that the measurements form a value tuple of the gas mixture in a thermodynamic state. The measurement of the viscosity and the density is implemented, for example, with a vibronic sensor, in particular, an oscillating cantilever, surrounded by the gas mixture.

In a step 20, the hydrogen fraction of the gas mixture is determined, on the basis of the heat conductivity measurement and associated pressure and temperature measurements, in particular, as a linear function of thermal conductivity at standard conditions, which is calculated here in accordance with equation 1.

In a step 30, the mean molar mass of the gas mixture is determined in accordance with equation 5 on the basis of the density measurement and the associated pressure and temperature measurements.

In a step 40, the mean molar mass of a residual gas mixture freed of the hydrogen is calculated on the basis of the mean molar mass of the gas mixture and of the hydrogen fraction.

In a step 50, the Wobbe index of the residual gas mixture is determined on the basis of the viscosity.

In a step 60, the calorific value of the residual gas mixture is determined in accordance with equation 4 on the basis of the mean molar mass of the residual gas mixture and of the Wobbe index of the residual gas mixture.

Optionally, in a step 70, the total calorific value of the gas mixture can be determined in accordance with equation 10 on the basis of the calorific value of the residual gas mixture and the hydrogen fraction.

As a further option, the inert gas fraction $X_{inert}$ of the gas mixture can be determined in a step 80, details of which are shown in the flow diagram in FIG. 6b.

First, in a step 82, a second calorific value for the residual gas mixture is determined, on the basis of the mean molar mass of the residual gas mixture, in accordance with equation 7.

Next, in a step 84, the inert gas fraction $X_{inert\text{-}R\text{-}C}$ of the residual gas mixture is calculated in accordance with equation 8 on the basis of the ratio of the second calorific value for the residual gas mixture to the calorific value determined via the Wobbe index.

In a step 86, the inert gas fraction of the gas mixture is calculated from this in accordance with equation 9.

Figure 7:
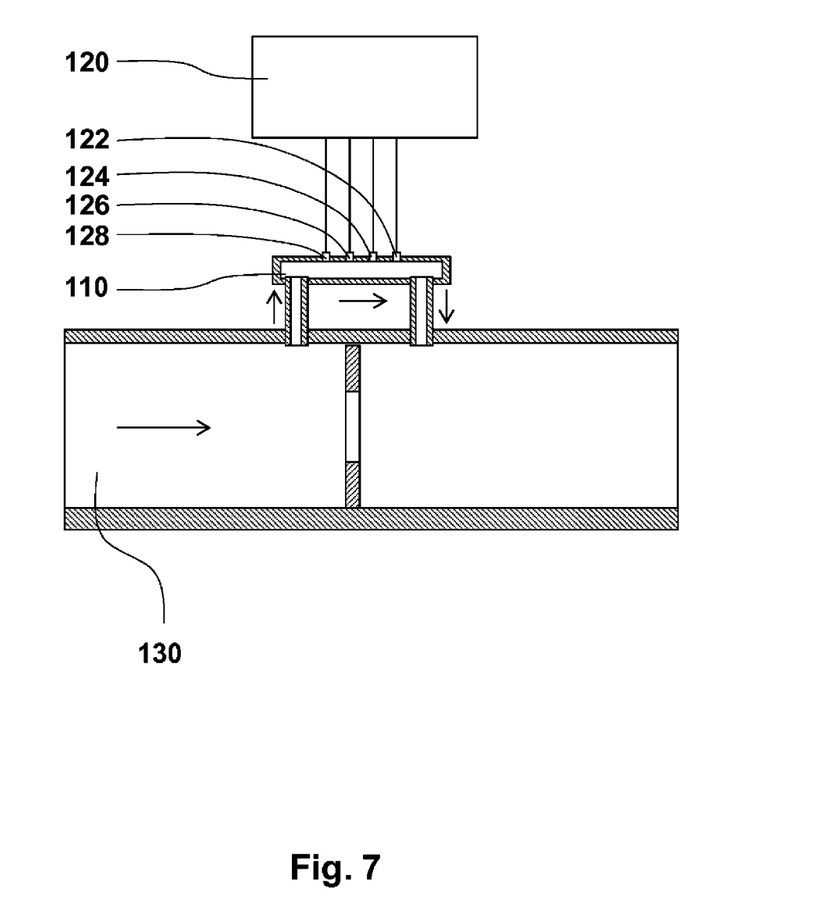
FIG. 7 shows an embodiment of an apparatus for carrying out method according to the present disclosure.

The exemplary embodiment of a device according to the invention for carrying out the method according to the invention comprises a measuring cell 110 through which the gas mixture can flow and in which are arranged sensor elements (only schematically illustrated here), viz., a cantilever 122 for determining the viscosity and the density of a gas mixture in the measuring cell, a pressure sensor 124, a temperature sensor 126, and a thermal conductivity sensor 128. The sensor elements are preferably implemented using MEMS technology. The individual sensor principles are known per se to the person skilled in the art and need not be explained in more detail here. The apparatus further comprises an operation and evaluation unit 120 for driving the sensor elements, for evaluating their signals in order to determine the primary measurands, such as viscosity, pressure, temperature, thermal conductivity, and density, and for determining the mean molar mass, the hydrogen fraction, the Wobbe index and/or the calorific value and/or the inert gas fraction of a gas mixture flowing through the measuring cell 110. For this purpose, the operating and evaluating unit comprises a computation unit which can be of compact or modular design and can, in particular, comprise modules spatially separated from one another. The measuring cell 110 is connected, in particular, in a bypass arrangement to a gas line 130, wherein a volume flow of the gas mixture can be driven through the measuring cell 110 by means of a pressure differential across the measuring cell 110, e.g., by virtue of a diaphragm or a Venturi nozzle in the pipeline, or by means of a pump (not depicted here).

The invention claimed is:

1. A method for determining properties of a hydrocarbon-containing gas mixture including natural gas or biogas, comprising:
    allowing the gas mixture to flow through a measuring arrangement;
    measuring a pressure- and temperature-dependent thermal conductivity, an associated temperature measurement, and an associated pressure measurement of the gas mixture resulting in a thermal conductivity value, wherein the thermal conductivity value is determined by at least one sensor of the measuring arrangement;
    calculating a hydrogen fraction of the gas mixture as a function of the thermal conductivity value, the associated temperature measurement, and the associated pressure measurement;
    measuring a pressure- and temperature-dependent density of the associated temperature measurement and the associated pressure measurement of the gas mixture, resulting in a density measurement, wherein the density measurement is based on the at least one sensor of the measuring arrangement;
    calculating a value for a mean molar mass or a standard density of the gas mixture as a function of the density measurement, the associated temperature measurement, and the associated pressure measurement;
    calculating a value for the mean molar mass or the standard density of a residual gas mixture reduced by the hydrogen fraction on the basis of the mean molar mass or the standard density of the gas mixture and of the hydrogen fraction;
    measuring a pressure-dependent and temperature-dependent viscosity, the associated temperature measurement, and the associated pressure measurement of the gas mixture, resulting in a viscosity measurement, wherein the viscosity measurement is based on the at least one sensor of the measuring arrangement;
    calculating a value for the Wobbe index of the residual gas mixture as a function of the viscosity measurement, the associated pressure measurement, and the associated temperature measurement;
    calculating a first value for the calorific value of the residual gas mixture as a function of the mean molar mass or the standard density of the residual gas mixture and of the Wobbe index of the residual gas mixture;
    identifying a composition of gases of the gas mixture as a function of the calorific value; and
    monitoring energy consumption, or controlling chemical processing, combustion, or delivery of the gas mixture through a pipeline, based on the identified composition.

2. The method according to claim 1, further including:
    determining an inert gas fraction of the residual gas mixture on the basis of the first value for the calorific value and the mean molar mass or the standard density of the residual gas mixture.

3. The method of claim 2, wherein determining the inert gas fraction includes:
    determining a second value for the calorific value on the basis of the mean molar mass and the standard density of the residual gas mixture using a function independent of the Wobbe index; and
    determining the inert gas fraction as a function of the first value for the calorific value of the residual gas mixture and the second value for the calorific value of the residual gas mixture.

4. The method of claim 3, wherein the determination of the inert gas fraction is based upon a ratio between the second value for the calorific value of the residual gas and the first value for the calorific value of the residual gas mixture.

5. The method of claim 2, further including:
    determining a value for an inert gas fraction of the gas mixture on the basis of the value for the inert gas fraction of the residual gas mixture.

6. The method of claim 2, wherein the inert gas fraction is determined under the assumption that an inert gas includes carbon dioxide and nitrogen.

7. The method of claim 1, wherein determining the value for the Wobbe index is preceded by determining a standard viscosity value of the gas mixture that the gas mixture would have at a standard temperature and a standard pressure, on the basis of the viscosity measurement, the associated temperature measurement, and the associated pressure measurement, wherein the Wobbe index is determined by means of the standard viscosity value of the gas mixture.

8. The method of claim 7, wherein the standard viscosity value and the standard density of the gas mixture are determined by a vibronic sensor, wherein the vibronic sensor has at least one oscillating measuring tube that is flowed through and/or at least one oscillator surrounded by the gas mixture.

9. The method of claim 1, further including:
    determining a calorific value of the gas mixture on the basis of the value for the hydrogen fraction, of a specific calorific value of hydrogen, and of the calorific value of the residual gas mixture.

10. The method of claim 1, wherein, to determine a molar mass of the gas mixture, a value for the standard density of the gas mixture is first determined under standard conditions on the basis of the pressure- and temperature-dependent density measurement of the associated temperature measurement and of the associated pressure measurement of the flowing gas mixture.

11. A device for determining properties of a hydrocarbon-containing gas mixture, including:
    a measuring arrangement through which the gas mixture can flow, the measuring arrangement including:
        a temperature sensor;
        a pressure sensor;
        at least a vibronic sensor for determining a viscosity measurement and a density measurement of the gas mixture;
        a thermal conductivity sensor; and
        an evaluation unit for calculating properties of the gas mixture;
    the evaluation unit configured to:
    measure pressure- and temperature-dependent thermal conductivity, an associated temperature measurement, and an associated pressure measurement of the gas mixture resulting in a thermal conductivity value, wherein the thermal conductivity value is determined by least one sensor of the measuring arrangement;
    calculate a hydrogen fraction of the gas mixture as a function of the thermal conductivity value, the associated temperature measurement, and the associated pressure measurement;
    measure a pressure- and temperature-dependent density of the associated temperature measurement and the associated pressure measurement of the gas mixture, resulting in a density measurement, wherein the density measurement is based on the at least one sensor of the measuring arrangement;
    calculate a value for a mean molar mass or a standard density of the gas mixture as a function of the density measurement, the associated temperature measurement, and the associated pressure measurement;
    calculate a value for the mean molar mass or the standard density of a residual gas mixture reduced by the hydrogen fraction on the basis of the mean molar mass or the standard density of the gas mixture and of the hydrogen fraction;
    measure a pressure-dependent and temperature-dependent viscosity, the associated temperature measurement, and the associated pressure measurement of the gas mixture, resulting in a viscosity measurement, wherein the viscosity measurement is based on the at least a vibronic sensor of the measuring arrangement;
    calculate a value for the Wobbe index of the residual gas mixture as a function of the viscosity measurement, the associated pressure measurement, and the associated temperature measurement;
    calculate a first value for the calorific value of the residual gas mixture as a function of the mean molar mass or the standard density of the residual gas mixture and of the Wobbe index of the residual gas mixture;
    identify a composition of gases of the gas mixture as a function of the calorific value; and
    monitor energy consumption, or control chemical processing, combustion, or delivery of the gas mixture through a pipeline, based on the identified composition.

12. The device of claim 11, wherein the vibronic sensor has at least one flow-through, oscillatable measuring tube and/or at least one oscillator surrounded by the flowing gas mixture.

* * * * *